(12) United States Patent
Urano et al.

(10) Patent No.: US 8,477,302 B2
(45) Date of Patent: Jul. 2, 2013

(54) DEFECT INSPECTION APPARATUS

(75) Inventors: Yuta Urano, Yokohama (JP); Toshiyuki Nakao, Yokohama (JP); Yoshimasa Oshima, Yokohama (JP); Akira Hamamatsu, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 226 days.

(21) Appl. No.: 12/412,776

(22) Filed: Mar. 27, 2009

(65) Prior Publication Data
US 2009/0279081 A1  Nov. 12, 2009

(30) Foreign Application Priority Data
Mar. 28, 2008 (JP) ................................. 2008-085167

(51) Int. Cl.
*G01N 21/00* (2006.01)
(52) U.S. Cl.
USPC ..................................... 356/237.5; 356/237.4
(58) Field of Classification Search
USPC .......................................... 356/237.1–237.6
See application file for complete search history.

(56) References Cited

U.S. PATENT DOCUMENTS

| | | | |
|---|---|---|---|
| 2004/0061851 | A1 | 4/2004 | Isozaki et al. |
| 2005/0110986 | A1* | 5/2005 | Nikoonahad et al. ...... 356/237.2 |
| 2007/0019185 | A1* | 1/2007 | Hamamatsu et al. ...... 356/237.2 |
| 2007/0121111 | A1* | 5/2007 | Blumenfeld et al. ......... 356/318 |
| 2007/0229813 | A1* | 10/2007 | Miyakawa et al. ........ 356/237.3 |
| 2009/0066941 | A1 | 3/2009 | Togashi et al. |

FOREIGN PATENT DOCUMENTS

| | | |
|---|---|---|
| JP | 09-304289 | 11/1997 |
| JP | 2000-162141 | 6/2000 |
| JP | 2001-235429 | 8/2001 |
| JP | 2002-277399 | 9/2002 |
| JP | 2007-273879 | 10/2007 |
| JP | 2008-14849 | 1/2008 |

OTHER PUBLICATIONS

"Light Scattering by a Sphere on a Substrate", Bobbert et al, Physica 137A (1986) 209-242, North-Holland, Amsterdam Elsevier Science Publishers B.V.

* cited by examiner

*Primary Examiner* — Tri T Ton
(74) *Attorney, Agent, or Firm* — Antonelli, Terry, Stout & Kraus, LLP.

(57) ABSTRACT

A defect inspection apparatus for inspecting a surface of a sample includes a stage for holding the sample, an illumination optical system that irradiates a laser beam to form a linear illuminated area on the surface of the sample, a detection optical system, and a signal processing system. The detection optical system includes a detector device having a plurality of pixels for detecting light scattered from the linear illuminated area of the surface of the sample, and that outputs in parallel a plurality of detection signals having mutually different sensitivities acquired from the plurality of pixels of the detector device. The signal processing system selects an unsaturated detection signal from the plurality of detection signals and detects a defect in accordance with the selected detection signal.

18 Claims, 13 Drawing Sheets

(a) t=t1

(b) t=t2

(c) t=t3

(d) t=t4

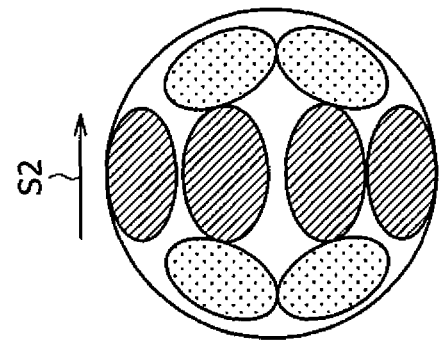
FIG. 7A  FIG. 7B  FIG. 7C
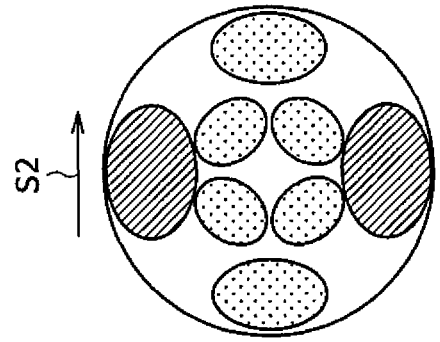
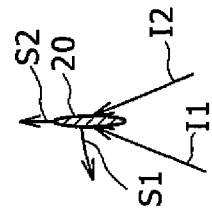
FIG. 8A
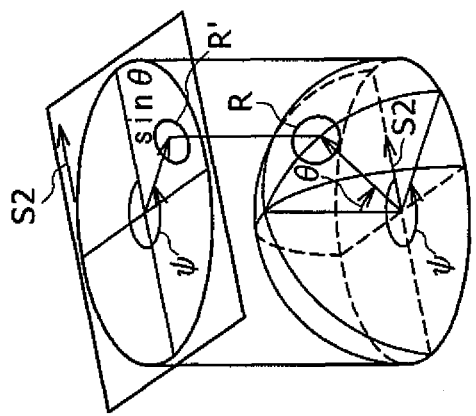
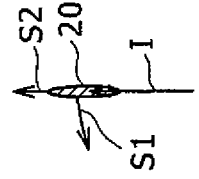
FIG. 8B FIG. 9A    FIG. 9B
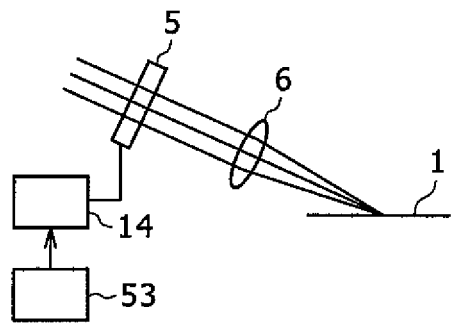
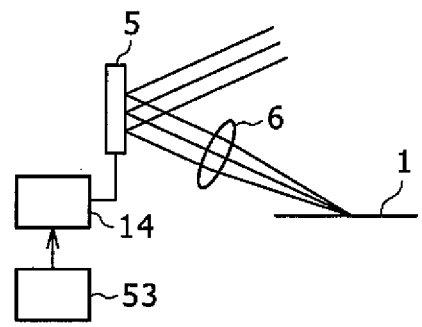
FIG. 9C    FIG. 9D    FIG. 9E
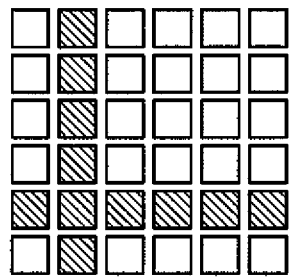
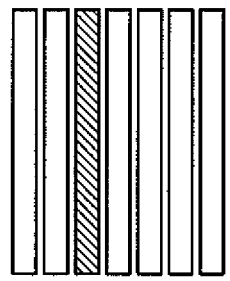
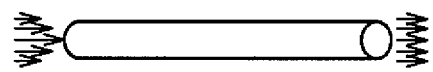
FIG. 10
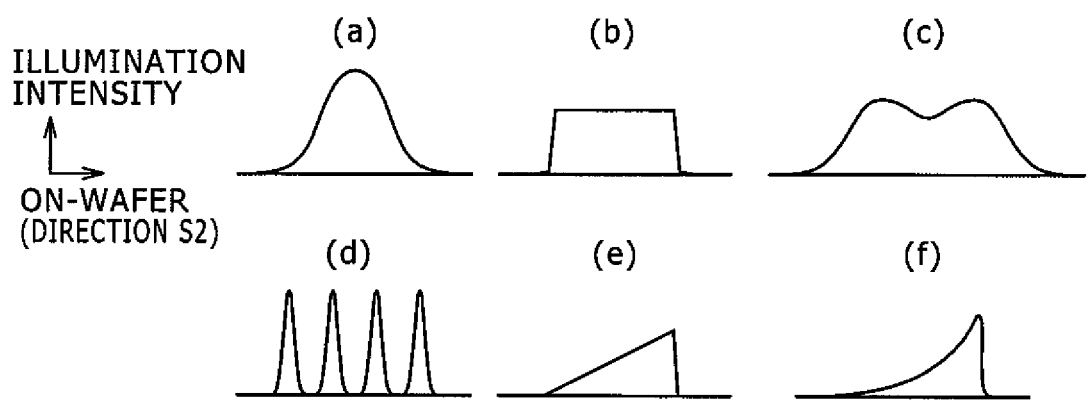

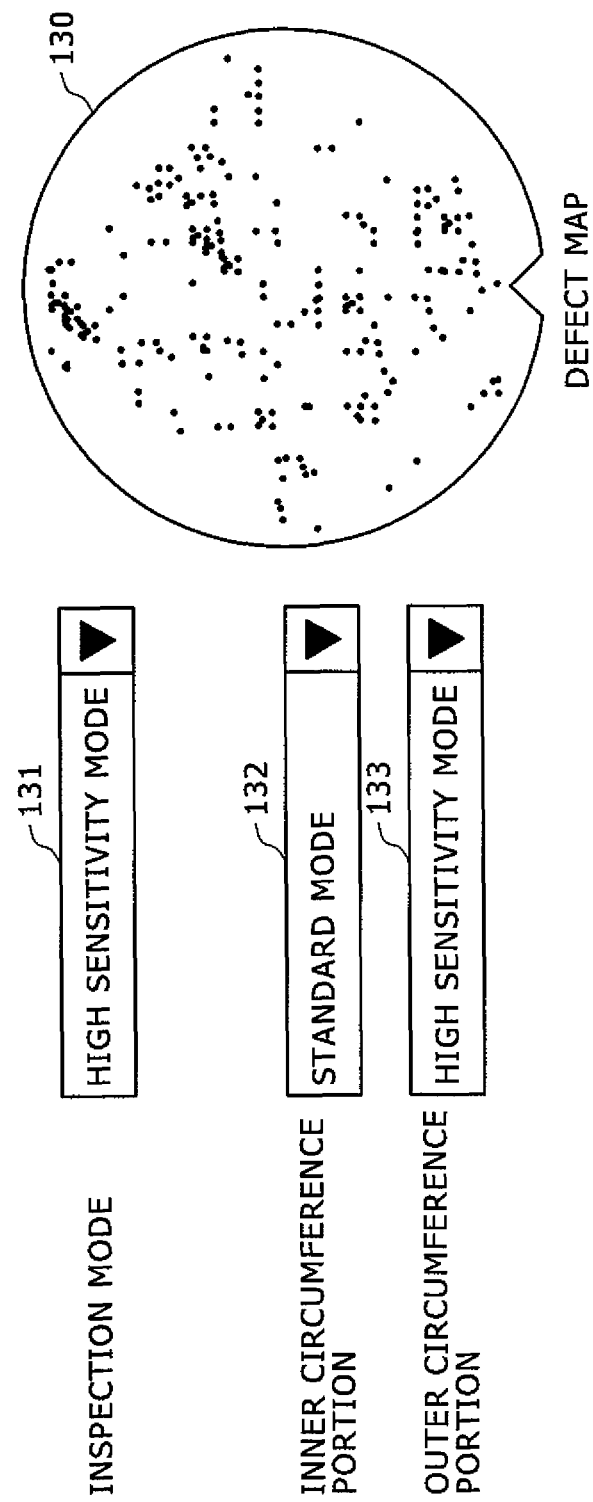

DEFECT INSPECTION APPARATUS

INCORPORATION BY REFERENCE

The present application claims priority from Japanese Patent application No. 2008-085167 filed on Mar. 28, 2008, the contents of which is hereby incorporated by reference herein.

CROSS REFERENCE TO RELATED APPLICATION

The application is related to U.S. application Ser. No. 12/109,548, filed Apr. 25, 2008 and U.S. application Ser. No. 12/362,950, filed Jan. 30, 2009 by some of the inventors herein.

BACKGROUND

In a manufacturing line for, for example, semiconductor substrates or thin film substrates, inspection of defects present on the semiconductor substrate is performed to maintain and improve the production yield of the products. As conventional techniques, those described in Patent Publications 1 (Japanese Unexamined Patent Application Publication No. 09-304289) and 2 (Japanese Unexamined Patent Application Publication No. 2000-162141) are known. In order to detect a respective small defect, the inspection is performed in the manner that a laser beam focused to several tens of micrometers ($\mu$m) is irradiated onto to the surface of the sample, and light scattered from a defect is focused and detected.

In connection with the above-described method, a calculation is utilized method as described in Non-patent Publication 1 (P. A. Bobbert and J. Vlieger, "Light scattering by a sphere on a substrate", Physica A, Volume 137, Issue 1-2, p. 209-242 (1986)). According to the technique, in a case where illumination light is irradiated on sphere particulates on a flat metallic dielectric member, the calculation method calculates the intensity and angular distribution of light scattered from the sphere particulates.

The technique for LSI wiring integration advances year by year, and the sizes of respective detection-target defects are now approaching a detection limit of optical inspection. According to the semiconductor road map, the defect detection capability is required to detect a defect having the size of 32.5 nm in 2007, and to detect a defect having the size of 20 nm or less in 2011 or subsequent years.

In order to achieve high speed inspection of a small defect, an amount of scattered light sufficient to enable the detector device to detect the defect has to be acquired from the defect. Hence, in order to achieve the inspection, it is effective to provide high-illuminance illumination by using a high power light source. However, when the illuminance is excessively increased, the amount of heat in the irradiated area is increased to the extent of damaging the LSI substrate. Hence, sensitivity improvement by increasing the illuminance is limited.

Further, in the case of an apparatus configuration arranged to be capable of detection of light scattered from a small defect, there occurs a large amount of light scattered from large-size or intermediate-size defects also present in the sample. Hence, the output power is saturated when those large or intermediate-size defects are detected by the same detector device used to detect the small defect. For example, the amount of light scattered from a particulate having a size of 500 nm is about 1,000,000 times as large as the amount of light scattered from a particulate having a size of 20 nm. Hence, in the event of detecting the latter light with use of a dynamic range (60 dB to 80 dB) of an ordinary photodetector device (such as a photoelectron multiplier tube or photodiode), a signal of the former light is saturated. When the output of the detector is saturated, a correct amount of scattered light is unknown, therefore making it difficult to achieve the calculation of the defect size in accordance with the amount of scattered light. Further, even in the case of identification of a defect position by use of, for example, the center of gravity of a defect waveform in accordance with a defect scatter signal, there is posed problems of, for example, deterioration in the accuracy of defect coordinate calculation due to saturation of the signal.

SUMMARY

The present invention is directed to solving the problems as described above, thereby to provide a defect inspection method and apparatus capable of performing small defect detection and high accuracy calculation of the defect size or defect coordinate, even for a large defect.

According to one aspect of the present invention, there is provided a defect inspection apparatus for inspecting a surface of a sample, including a stage for holding the sample; an illumination optical system that irradiates a laser beam to form a linear illuminated area on the surface of the sample; a detection optical system that includes a detector device including a plurality of pixels for detecting light scattered from the linear illuminated area of the surface of the sample, and that outputs in parallel a plurality of detection signals having mutually different sensitivities acquired from the plurality of pixels of the detector device; and a signal processing system that selects an unsaturated detection signal from the plurality of detection signals and that detects a defect in accordance with the selected detection signal. The plurality of detection signals output in parallel from the detection optical system may be, respectively, based on scattered light detected through multi-time illumination provided onto a same area of the surface of the sample. Further, the plurality of pixels of the detector device may have mutually different sensitivities.

The illumination optical system may irradiate the laser beam so that an illuminance distribution in the linear illuminated area of the surface of the sample has an inclination. Further, the illumination optical system may irradiate the laser beam so that an illuminance distribution in the linear illuminated area of the surface of the sample includes a distribution maximized in units of a position corresponding to the plurality of pixels of the detector device. Also, the illumination optical system may irradiate the laser beam so that an illumination incident angle is 75 degrees or greater with respect to the surface of the sample.

An optical axis of the detection optical system may be present in a plane substantially perpendicular to a longitudinal direction of the linear illuminated area. The defect inspection apparatus may further including an oblique detection system having an optical axis inclined from a direction substantially perpendicular to the longitudinal direction of the linear illuminated area.

The signal processing system may calculate a defect size by using the selected detection signal.

The defect inspection apparatus may further includes a review optical system that monitors the illuminance distribution in the linear illuminated area of the surface of the sample.

According to another aspect of the present invention, there is provided a defect inspection method for inspecting a surface of a sample, including a first step that provides multi-time irradiation of a laser beam onto a same area of a surface of the sample; a second step that detects scattered light from the same area through respective-time irradiation of the multi-time irradiation to thereby acquire plurality of detection signals having mutually different effectual sensitivities; and a third step that selects an unsaturated detection signal from the plurality of detection signals and that detects a defect in accordance with the selected detection signal. The laser beam may be irradiated to form a linear illuminated area on the surface of the sample. Further, the laser beam may be irradiated so that an illuminance distribution in the linear illuminated area of the surface of the sample has an inclination. In the second step, the scattered light corresponding to the each-time irradiation may be detected from the same area through mutually different pixels of a detector device including a plurality of pixels, and the plurality of pixels may have mutually different sensitivities.

BRIEF DESCRIPTIONS OF THE DRAWINGS

Figure 6A:
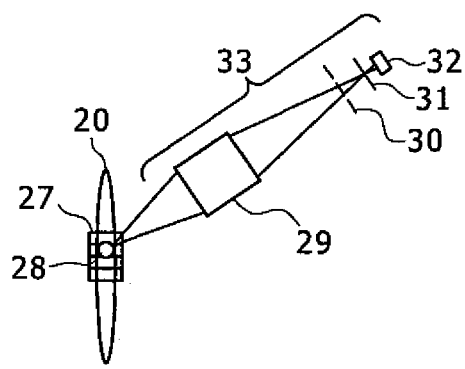
Figure 6B:
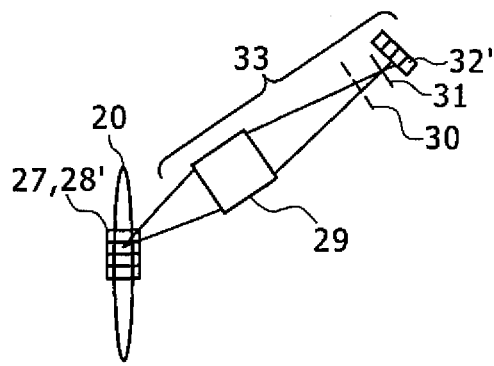

FIGS. 6A and 6B includes configuration views respectively showing the configurations of oblique detection systems.

FIGS. 7A-7C include schematic views showing detection angular ranges exhibited by the detection optical system and the oblique detection system.

FIGS. 8A and 8B include schematic views each showing the relation between the azimuth of the oblique illumination and the scan direction.

FIGS. 9A-9E include configuration views and schematic views showing the configurations of illuminance distribution control elements and illuminance distribution control methods.

FIG. 10 includes distribution diagrams (a)-(f) respectively showing illuminance distributions achieved by a illumination optical system.

Figure 11:
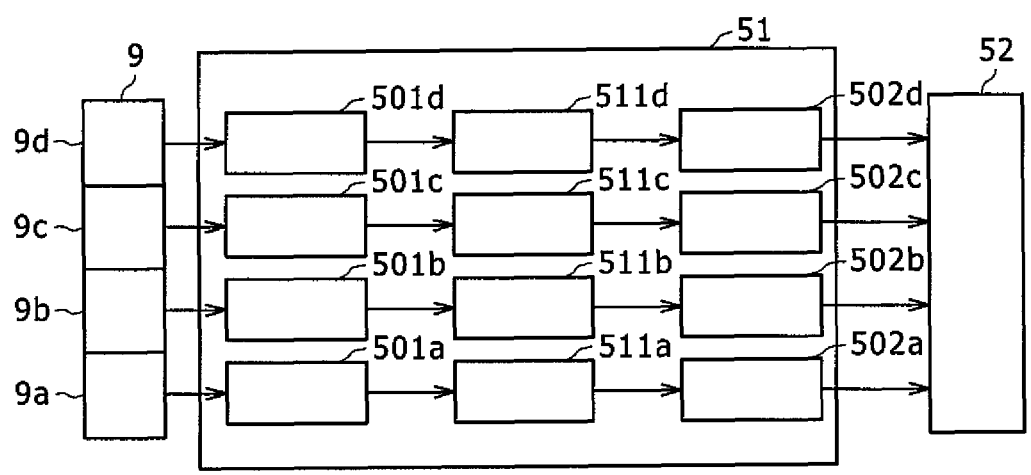

FIG. 11 is an example of a block diagram showing the configuration of an analog processing section.

Figure 12:
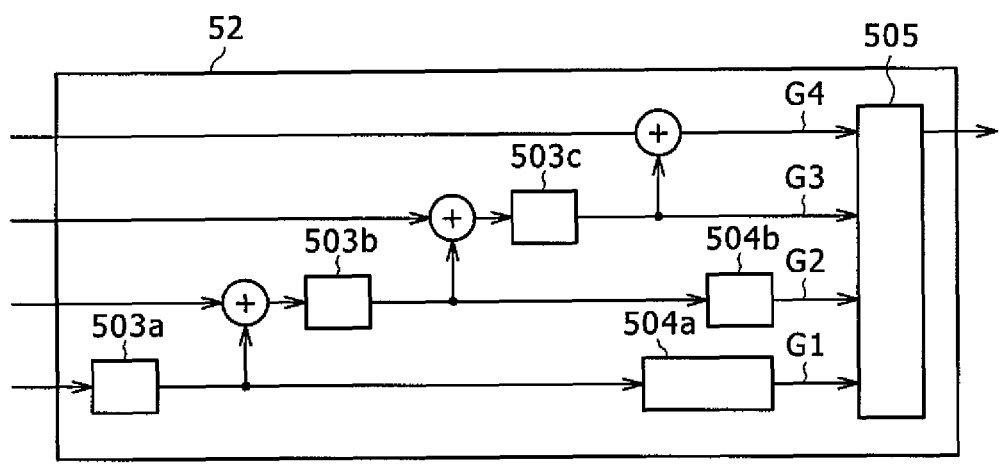

FIG. 12 is an example of a block diagram showing a digital processing section.

Figure 13A:
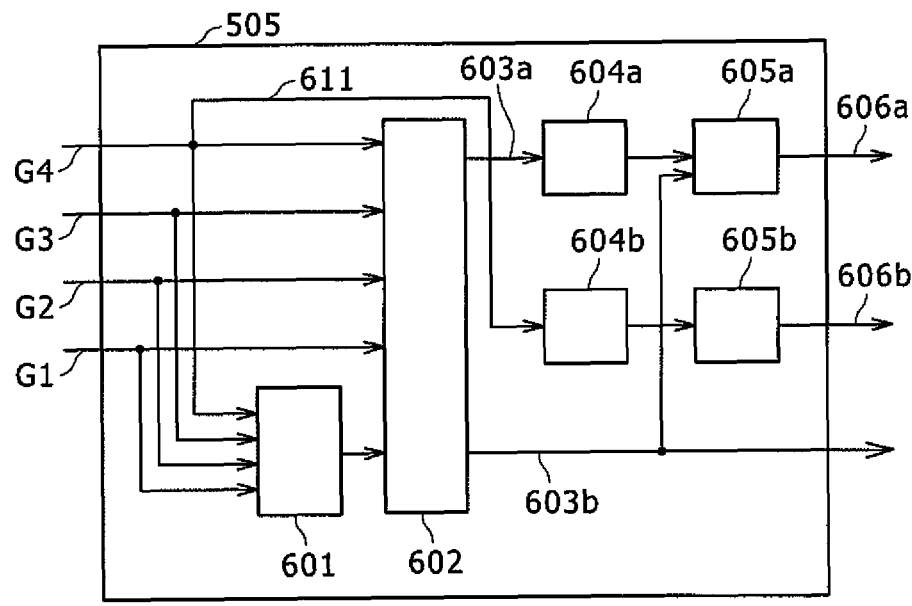
Figure 13B:
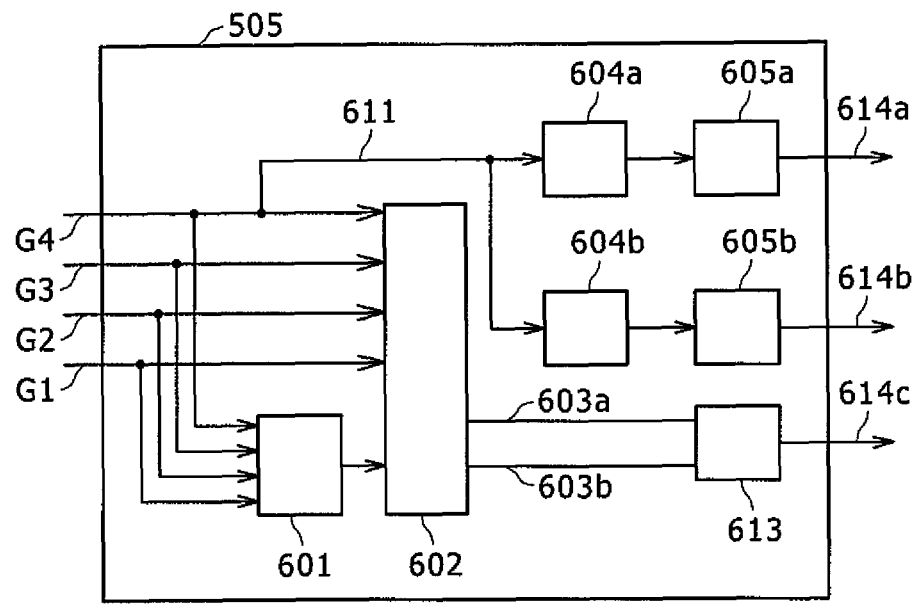

FIGS. 13A and 13B are examples of block diagrams showing the configuration of a determination processing section.

Figure 14A:
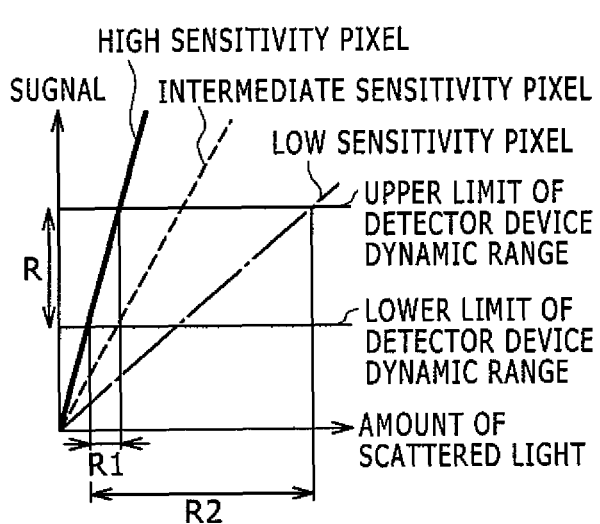
Figure 14B:
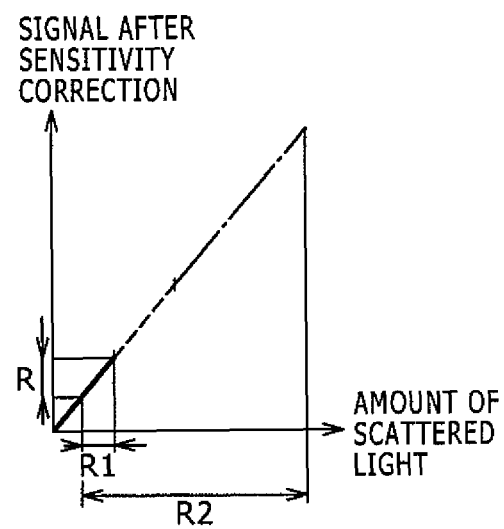
Figure 14C:
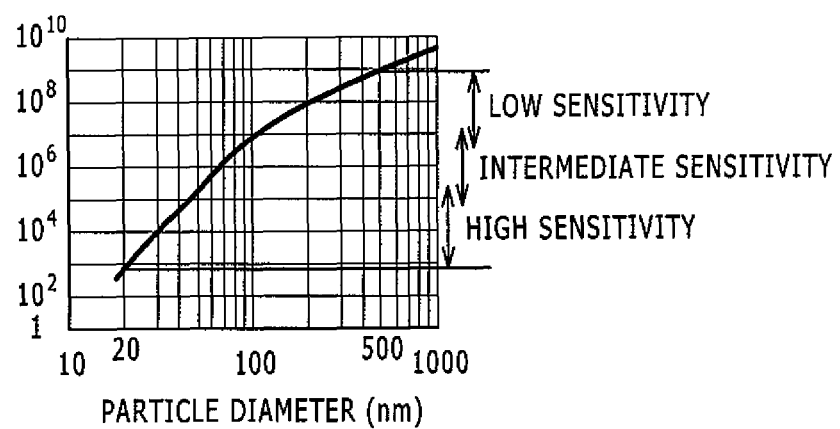

FIGS. 14A-14C include graphs showing the relation among an amount of scattered light, detection signal, and particle diameter.

Figure 15B:
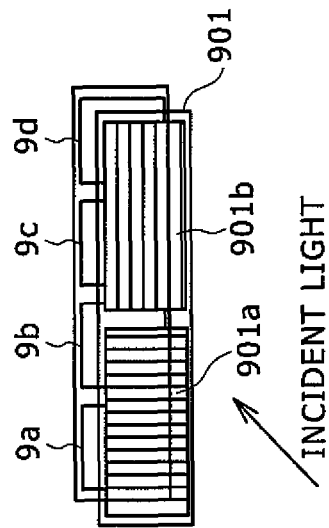
Figure 15A:
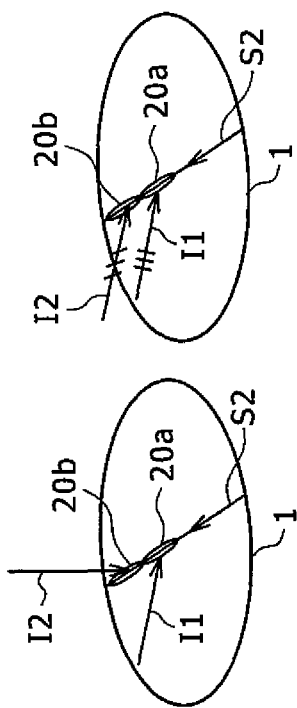
Figure 15C:
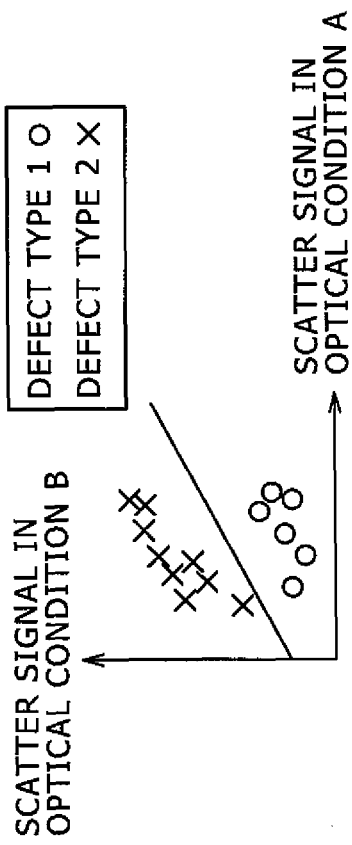

FIGS. 15A-15C include configuration views showing a device that acquires detection signals under multiple mutually-different optical conditions, and a scattergram showing a defect classification method using the detection signals.

Figure 16A:
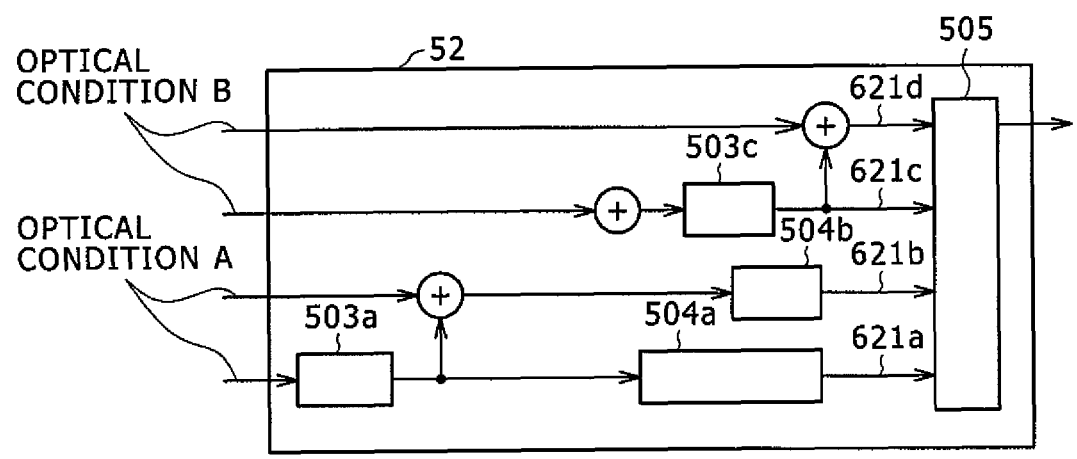
Figure 16B:
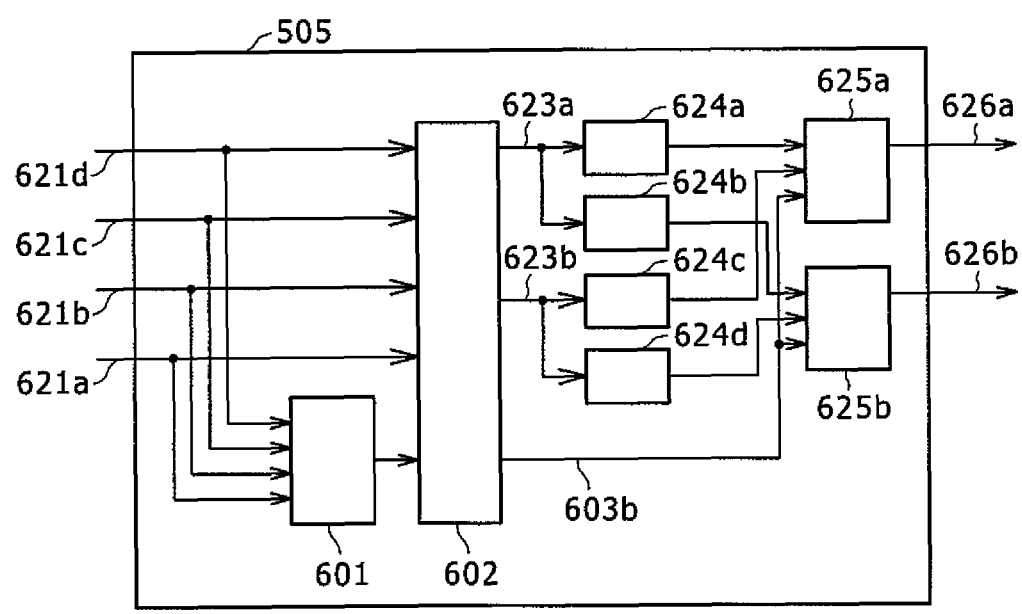

FIGS. 16A and 16B include block diagrams showing the configurations of processing sections that processes the detection signals under the multiple mutually different optical conditions.

Figure 17A:
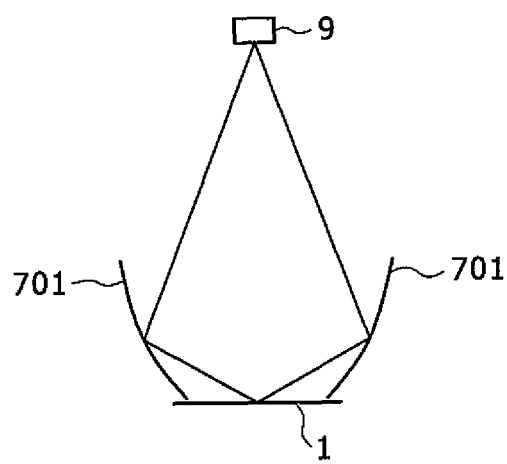
Figure 17B:
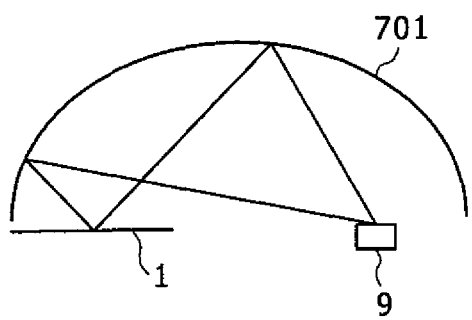
Figure 17C:
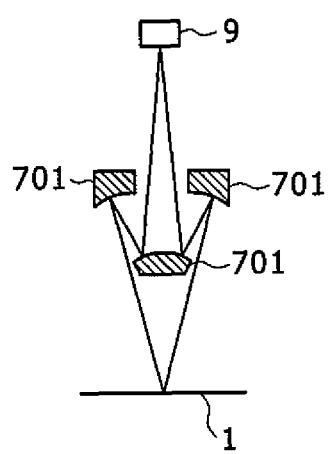

FIGS. 17A-17C include configuration views showing example configurations of imaging systems each formed using a reflection optical system.

Figure 18:
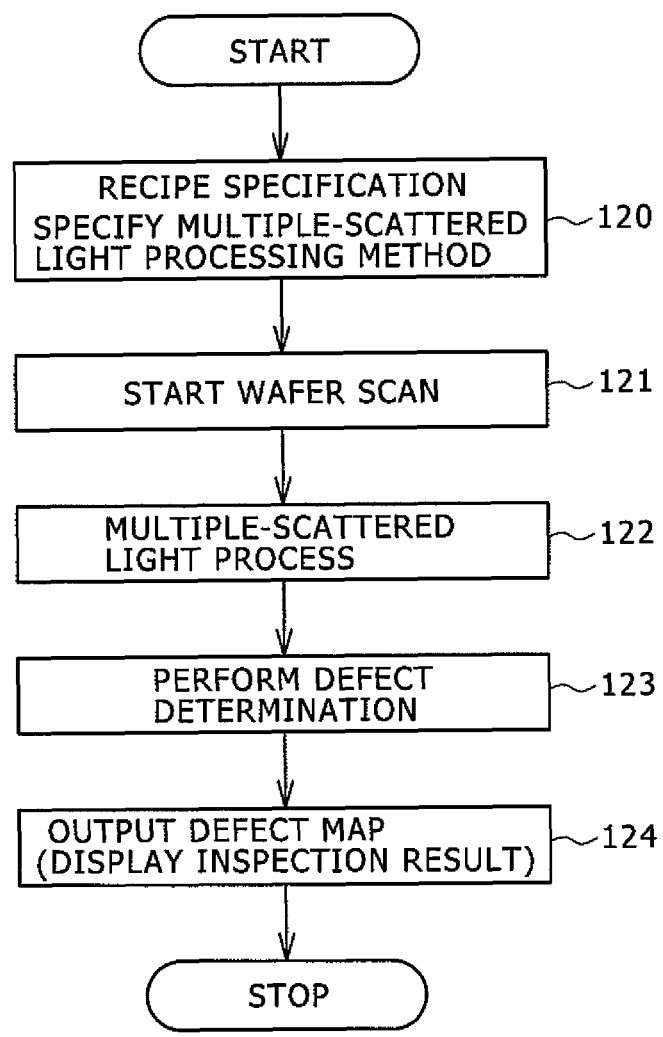

FIG. 18 is an example of a flow diagram showing the flow of a defect detection process.

FIG. 19 is an example of a view showing a user interface that displays recipe specifications and the inspection result.

DESCRIPTION OF THE PREFERRED EMBODIMENTS

First Embodiment

Figure 1:
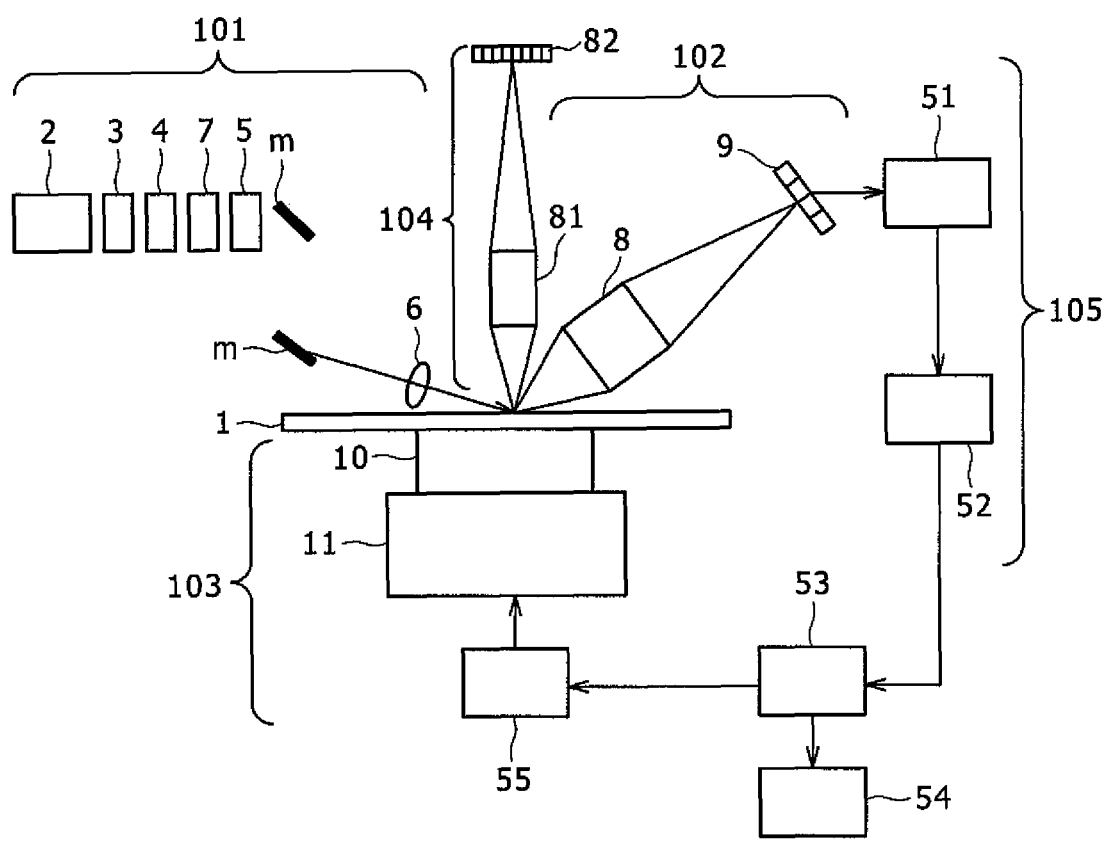
FIG. 1 is an example of a schematic configuration view showing the overall configuration of an embodiment of the present invention.

With reference to FIG. 1, a first embodiment of a defect inspection apparatus of the present invention is configured using at least an illumination optical system 101 that irradiates illumination light onto a wafer 1; a detection optical system 102 that detects scattered light of the illumination light from the wafer 1 from a first direction; an oblique detection optical system 33, as shown in FIGS. 6A and 6B, that directs scattered light from the wafer 1 from a second direction; a stage 103 capable of mounting the wafer 1; a signal processor section 105 that process a detection signal obtained in the detection optical system 102; a total control section 53; and a display section 54. However, the defect inspection apparatus is configured further using, by necessity, a review optical system 104 that monitors illuminance distribution in an illuminated area of the wafer 1.

The illumination optical system 101 is appropriately configured using a laser light source 2, an attenuator 3, a polarizing element 4, a beam expander 7, an illuminance distribution control element 5, a reflection mirror m, and a collector lens 6. A laser beam emitted from the laser light source 2 is adjusted by the attenuator 3 to a desired beam intensity, is then adjusted by the polarizing element 4 to a desired polarized state, and is then adjusted by the beam expander 7 to a desired beam diameter. Then, the laser beam is irradiated onto an inspection-target area of the wafer 1 through the reflection mirror m and the collector lens 6. The illuminance distribution control element 5 is used to control intensity distribution of the illumination on the wafer 1. As the laser light source 2, in order to detect a small defect near the wafer surface, there is used a light source of the type that oscillates a short-wavelength ultraviolet or vacuum ultraviolet laser beam and that is capable of producing a high output power of 1 W (watt) or higher. In order to detect an intra-wafer defect, a light source of the type that oscillates a visible or infrared laser beam is used.

As the collector lens 6, a cylindrical lens is used. Thereby, an area (view field) to be irradiated with the laser beam on the wafer surface is rendered to be a shape that is long in one direction and is short in the direction perpendicular thereto. Alternatively, an anamorphic optical system configured from multiple prisms can be used. In this case, after the beam diameter is varied along one direction in the plane perpendicular to the optical axis, the optical system illuminates shape that is long in one direction on the wafer and is short in the direction perpendicular thereto. The anamorphic optical system is effective to facilitate optical axis adjustment.

Figure 2:
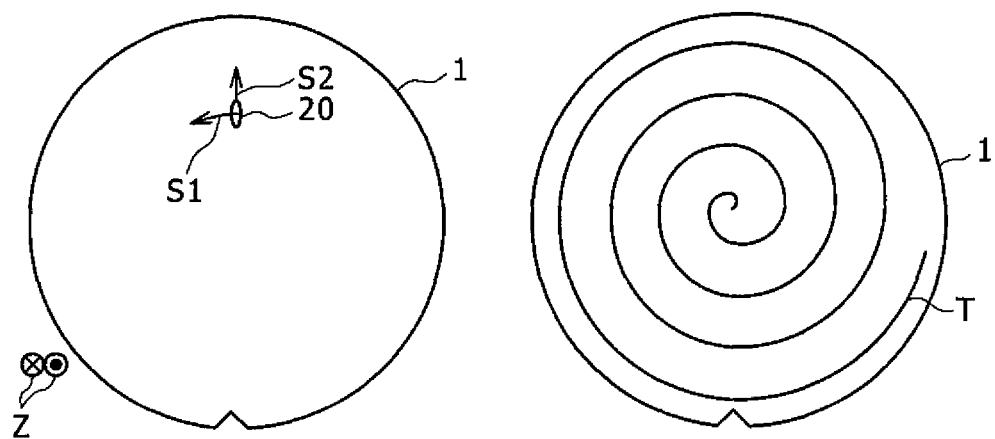
FIG. 2 is an example of a schematic view showing a scanning method of a sample.

The stage 103 is configured using a stage control section 55, a translation stage 11, a rotating stage 10, and a Z stage (not shown). FIG. 2 shows an illuminated area 20 on the wafer 1, the relation thereof with a scan direction associated with motions of the rotating stage 10 and the translation stage 11, and a trajectory of the illuminated area 20 rendered thereby on the wafer 1. The illuminated area 20 is scanned by the rotary motion of the rotating stage 10 along a circumferential direction S1 of a circle with the rotation shaft of the rotating stage 10 in the center, and is scanned by a translational motion of the translation stage 11 along a translation direction S2 of the translation stage 11. The illumination optical system 101 is configured so that the longitudinal direction of the illuminated area 20 is parallel to the translation direction S2, and concurrently, the illuminated area 20 is moved by scanning along the translation direction S2 to pass through the rotation shaft of the rotating stage 10. The movement of the Z stage corresponds to the height of the wafer 1, i.e., a normal line direction of the surface of the wafer 1. In the configuration described above, during one rotation of the wafer 1 in operative association with scanning along the circumferential direction S1, scanning along the translation direction S2 is performed by a distance less than or equal to a length of the illuminated area 20 in the longitudinal direction. In this case, the illuminated area 20 renders a spiral trajectory T, whereby the overall surface of the wafer 1 is scanned.

In the case where the ultraviolet light is irradiated on a small foreign matter having a size of 100 nm or less, when P polarization illumination is effected from an oblique direction obliquely inclined relative to the wafer surface normal line, large scattered light occurs. In particular, the scattered light becomes largest at an illumination incident angle of 75 degrees. Further, an angular distribution of the scattered light occurring in the event of illumination effected from the oblique direction is intensively biased at an oblique angle relative to the wafer surface normal line. In particular, the light is intensively emitted focusing on an angular range inclined 60 to 65 degrees relative to the wafer surface normal line. In the present embodiment, large scattered light is detected from the small foreign matter, so that the configuration is formed to perform the light detection from the oblique direction. These knowledges regarding the illumination angle dependency of scattering by the on-substrate particle and the angular distribution of the scattered light intensity can be obtained through the calculation in accordance with Non-patent Publication 1.

Figure 3A:
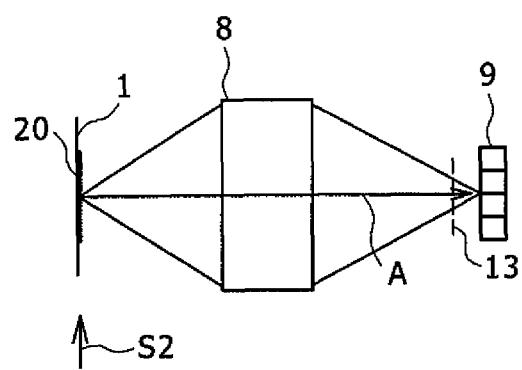
FIGS. 3A and 3B are examples of configuration views of the disposition a detection optical system.
Figure 3B:
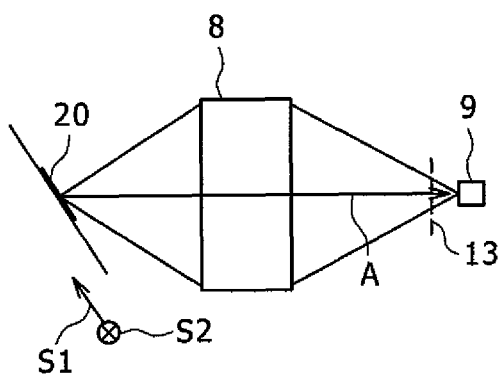

With reference to FIG. 3 (including FIGS. 3A and 3B), the detection optical system 102 is configured using an imaging system 8, a polarizing filter 13, and a linear array sensor 9. The polarizing filter 13 is removably mountable to an optical axis A, and is used to attenuate a scattered light component caused due to the wafer roughness portion, which can act as noise factors. FIG. 3A is a cross sectional view of a plane including the optical axis A and translation direction S2 of the imaging system 8. An image in the illuminated area 20 is imaged by the imaging system 8 on the linear array sensor 9. A longitudinal direction of the linear array sensor 9, that is, the direction of arrangement of multiple pixels, is arranged parallel to the translation direction S2, and corresponds to the longitudinal direction of the illuminated area 20. FIG. 3B is a cross sectional view of a plane inclusive of the optical axis A of the imaging system 8 and the circumferential direction S1. As described above, in order to obtain even larger scattered light from the foreign matter, it is effective that the optical axis A is inclined relative to the normal line direction of the surface of the water 1. When providing the oblong illumination of the ultraviolet light, the scattered light intensively occurs focusing on the angular range of from 60 degrees to 65 degrees. Hence, it is effective to form the configuration so that the above-described direction is included in a detection angular range of the imaging system 8.

FIG. 17 (including FIGS. 17A to 17C) shows example configurations of imaging systems 8 each formed using a reflection optical system 701. FIG. 17 shows example configurations each using an ellipsoidal mirror. In any one of the example configurations, an ellipsoidal first focal position is set as a position of irradiation of illumination light, and a second focal position is arranged on a light receiving surface of the linear array sensor 9. The configuration shown in FIG. 17A is suitable to guide scattered light emitted at small angle relative to the wafer plane. The configuration shown in FIG. 17B is suitable to guide scattered light emitted in a wide angular range to the linear array sensor 9 for detection of a small defect. The configuration shown in FIG. 17C is an example configuration formed according to a Schwarzschild optical system. The configuration is suitable to image-form scattered light on the linear array sensor 9 in the event of providing illumination with a short wavelength having a 200 nm wavelength or less.

Figure 4A:
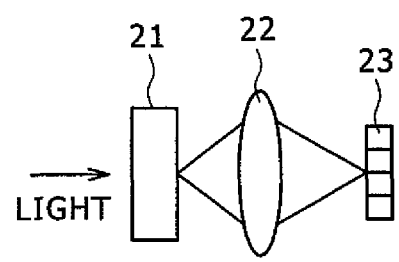
FIGS. 4A and 4B are examples of configuration views showing an example configuration of a linear sensor array.
Figure 4B:
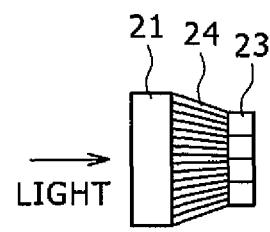
Figure 5A:
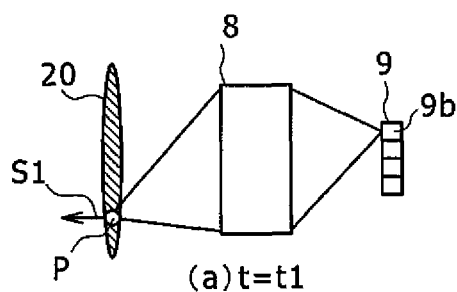
FIGS. 5A-5D are examples of schematic views showing a positional relationship on the sample between an illuminated area and the detection optical system.
Figure 5B:
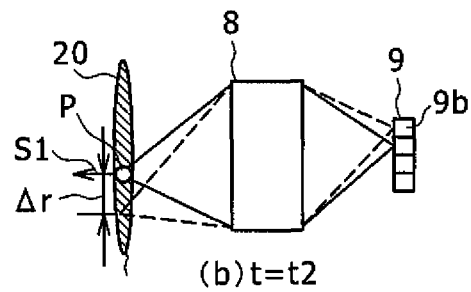
Figure 5C:
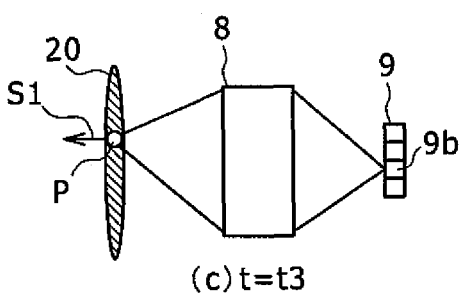
Figure 5D:
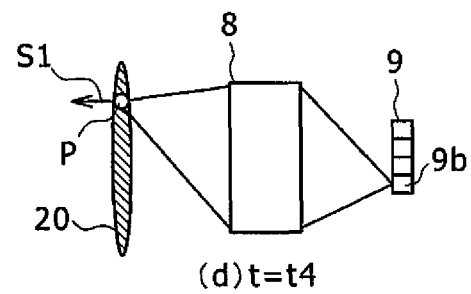

FIG. 4 (including FIGS. 4A and 4B) shows first and second example configurations of linear array sensors 9. The first example configuration of the linear array sensor 9 shown in FIG. 4A is formed using an image intensifier 21, a relay lens 22, and a photodiode array 23, and is suitable for detection of faint foreign matter scattered light. In the linear array sensor 9, incident light is amplified by the image intensifier 21, and the amplified light is re-image-formed on the photodiode array 23 through the relay lens 22. According to the configuration, faint foreign matter scattered light is detected with high sensitivity, and a per-pixel signal is output in parallel at high speed. The second configuration of the linear array sensor 9 shown in FIG. 4B is configured to operate in the manner that light amplified by the image intensifier 21 is output by a fiber image formation section 24 to the photodiode array 23. However, the configuration is not limited thereto. For example, when it is desired to simplify the configuration of the detection optical system 102, the linear array sensor 9 may be any one of a multi-anode photoelectron multiplier tube capable of parallel outputting signals with an electron multiplication function, and an avalanche photodiode array.

FIG. 5 (including FIGS. 5A to 5D) shows the positional relation among a defect position P, the illuminated area 20, and the detection optical system 102 on the wafer. For the sake of brevity, the respective examples will be described assuming that the linear array sensor 9 is formed from four pixels. The illuminated area 20 is image-formed on a light receiving surface of the linear array sensor 9 by the imaging system 8. In the event of time "t=t1"(FIG. 5A), the defect position P on the wafer is in a common usage relation with the positions of respective pixels 9a, and scattered light from the defect position P at the time point (t1) is detected at a pixel 9a. At a time "t=t2=t1+Δt" (FIG. 5B), as viewed from the perspective of the illuminated area 20, the defect position P is moved on the wafer by scanning in the direction S1, and is located in a position shifted by Δr relative to the time t1. The shift amount Δr corresponds to an inter-pixel interval on the light receiving surface of the linear array sensor 9, and the scattered light from the defect position P at this time point (t2) is detected at a pixel 9b. Similarly, at a time t3 (FIG. 5C), the scattered light from the defect position P is detected at a pixel 9c; and at a time t4 (FIG. 5D), the scattered light from the defect position P is detected at a pixel 9d.

Where a scan speed (angular velocity) in the scan direction S1 is ω, and a scan speed in the scan direction S2 is v, a time interval when the defect position P reaches the illuminated area 20 is represented by Equation 1 below, and the interval in the scan direction S2 is represented by Equation 2 below.

$$\Delta t = 2\pi/\omega \quad (1)$$

$$\Delta r = 2\pi v/\omega \quad (2)$$

Δr is determined from the inter-pixel interval in the linear array sensor 9 and the optical magnification of the imaging system 8. When the scan speeds w and v satisfying the relation of Equation 2 is specified, a scattered light signal from an identical portion of the wafer is output in units of the time interval Δt from each of the mutually different pixels. Addition and a parallel read process are applied to the above-described respective signal in the signal processor section 105, which is described further below. The identical portion on the wafer is irradiated multiple times, and the scattered light signals acquired in the respective operations of irradiation are added together. Thereby, a high sensitivity, wide dynamic range inspection can be implemented without causing thermal damage on the wafer due to high illuminance.

FIG. 6 (including FIGS. 6A and 6B) shows general configurations of the oblique detection optical system 33 (as examples). The oblique detection optical system 33 is configured appropriately using a collector lens 29, a polarizing filter 30, a field stop 31, and a point sensor 32. While the optical axis of the detection optical system 102 is present in the plane in the direction perpendicular to the longitudinal direction of the illuminated area 20, the optical axis of the oblique detection optical system 33 is oblique relative to the direction perpendicular to the longitudinal direction of the illuminated area 20. On the illuminated area 20, there is a view field 27 that corresponds to the linear array sensor 9 of the detection optical system 102. As shown in FIG. 6A, the collector lens 29, the field stop 31 and the point sensor 32 are configured and disposed to detect scattered light occurring from an area corresponding to an arbitrary one of the pixels of the linear array sensor 9 in the view field 27. The point sensor 32 includes a point sensor view field 28 in a detection position associated with an arbitrary pixel of the linear array sensor 9. In this configuration, scattered light emitted from the position is detected in the detection direction and angle different from those of the optical system 102, and a scattered light signal acquired is output.

FIG. 6B shows another example configuration of the oblique detection optical system 33. The example configuration shown in FIG. 6B is configured appropriately using the collector lens 29, the polarizing filter 30, the field stop 31, and a linear sensor 32'. The configuration is formed to cause the linear sensor 32' to detect the positions corresponding to the respective pixels of the linear array sensor 9 in the view field 27, Detection is performed from the detection oblique to the longitudinal direction of the illuminated area 20, so that the image plane inclined from the optical axis. The linear sensor 32' is inclined relative to the optical axis so as to correspond to the inclination, According to the configuration shown in FIG. 6A, the oblique detection optical system 33 can be configured to be compact at a low cost. According to the configuration shown in FIG. 6B, a signal associated with scattered light emitted along the direction perpendicular to the longitudinal direction of the illuminated area 20 is output from each of the mutually different pixels of the linear sensor 32' in units of the time interval Δt. The signal is subjected to processes, such as addition, saturation determination, selective use, are performed for the respective signal in the signal processor section 105, which is described further below. Thereby, a high sensitivity, wide dynamic range inspection can be implemented.

FIG. 7B shows the relation between angular components of scattered light detected by the respective detection optical system 102 and oblique detection optical system 33. FIG. 7A is an explanatory view of a displaying method for an angular range to be detected. FIG. 7A shows a hemisphere in which an equatorial surface corresponds to the wafer surface and the pole is set in the normal line direction of the wafer surface. The azimuth angle (longitude) with respect to the reference set to the scan direction S2 is represented by ψ, and the angle from the pole (polar angle) is represented by θ. An angular range for detection by either the detection optical system 102 or the oblique detection optical system 33 on the hemisphere is indicated by an area R.

FIG. 7 (including FIGS. 7B and 7C) shows representations of the hemisphere through parallel projection made on a plane parallel to the equatorial surface. In the drawing figures, the detection angular range corresponding to the detection optical system 102 is shown in a halftone display fashion with slanted lines, and a detection angular range corresponding to the oblique detection optical system 33 is shown in a halftone display fashion with dots.

As shown in FIG. 7, with the provision of multiple detection optical systems 102 and multiple oblique detection optical systems 33, a wide angular range can be covered, and hence various types of defects can be detected. Further, the angular distribution is different depending upon, for example, the defect type and the defect size. Hence, classification of the defect type and estimation of the defect size can be performed with high accuracy in the manner that the scattered light intensities at various angles are simultaneously detected by the multiple detection systems, and are processed by the signal processor section 105 described further below.

FIG. 7B shows one example of a detection system arrangement suitable to detect foreign matters in the range of from a small size to a large size. With the high sensitivity configuration of the detection optical system 102, scattered light components including angles θ ranging from 60 to 65 degrees are detected with a high NA (numerical aperture), a very small defect can be detected.

FIG. 7C shows one example of a detection system arrangement suitable COP defects (COP: crystal originated particle). The COP defect is a recess defect, such that scattered light having a low elevation angle (θ=large) is less likely to occur. Hence, in order to detect the COP defect, the high sensitivity configuration of the detection optical system 102 is used to detect a scattered light component having a high elevation angle (θ<30 degrees). Thereby, even defects inclusive of small COP defects can be detected. In the manner that scattered light components each having a low elevation angle permitting intensive scattered light of a small foreign matter are detected, synchronous detection of a small defect and a COP defect and classification thereof can be implemented. The positional relationship and the arrangement number of detection optical systems 102 and oblique detection optical systems 33 are not limited to those shown FIG. 7 and can be changed in various ways. For example, the configuration may be formed such that all the eight azimuthal sections as shown in FIG. 7C are configured using detection optical systems 102, and the arrangement number thereof can be increased or reduced.

FIG. 8 (including FIGS. 8A and 8B) shows the relation between the azimuth of oblique illumination by the illumination optical system 101 and the scan direction S1, S2.

FIG. 8A is an example case of providing illumination along an azimuth I parallel to the scan direction S2. In the case where misalignment or vibration in the height direction of the stage, a misalignment of the illuminated area 20 appears as error in defect detection coordinate. According to the configuration of FIG. 8A, the misalignment of the illuminated area 20 occurs in the direction S2 where the gradient of the illuminance distribution is slow. Hence, compared to the case where the misalignment occurs in the direction S1 where the gradient of the illuminance distribution is sharp, there is an advantage in that the error in the defect detection coordinate is reduced.

FIG. 8B shows another example in which the illumination azimuth is set to two azimuths, namely, azimuths 11 and 12.

This is implemented by separating the optical axis of the illumination optical system 101. In the case of inspection of a defect having anisotropy, such as scratch, caused in, for example, an abrading step, the amount of occurring scattered light greatly varies depending on the relation between the illumination azimuth and the defect azimuth, such that there occurs nonuniformity as a problem. However, in the case where, as shown in FIG. 8B, illumination is provided along two mutually different azimuths, fluctuation in inspection sensitivity associated with the defect azimuth can be suppressed, and hence robust inspection can be performed even for a defect having anisotropy.

Next, the configuration of the illuminance distribution control element 5 of the illumination optical system 101 and an illuminance distribution control method will be described with reference to FIG. 9 (including FIGS. 9A to 9E).

FIG. 9A is an example configuration using a transmission optical element as the illuminance distribution control element 5. The laser beam is emitted from the laser light source 2, is then adjusted by the configuration of the illumination optical system 101 to a desired intensity, polarized state, and beam diameter. Then, the beam is transmitted through the illuminance distribution control element 5 and is then guided onto the wafer 1 through the collector lens 6.

FIG. 9B shows an example configuration in the case where a reflection optical element is used as the illuminance distribution control element 5. As the illuminance distribution control element 5, there is used an optical element that includes a function that varies the intensity or phase of transmission light in units of a two-dimensional (FIG. 9C) or one-dimensional position (FIG. 9D) in a plane perpendicular to the optical axis of the transmission light. The relation thereof with the collector lens 6 is arranged to cause an image on a light transmission surface of the illuminance distribution control element 5 to be formed on the wafer 1. Thereby, an analog to a light intensity distribution modulated by the illuminance distribution control element 5 is projected onto the wafer 1. Alternatively, the distance from the collector lens 6 to a crosspoint between the upper surface of the wafer 1 and the optical axis and the distance from the collector lens 6 to the light transmission surface of the illuminance distribution control element 5 are both equalized to the focal distance of the collector lens 6. Thereby, a Fourier transformed image of an optical amplitude distribution on the light transmission surface of the illuminance distribution control element 5 is projected onto the wafer 1.

According to the configuration described above, an illuminance distribution corresponding to the transmittance and phase distributions provided from the illuminance distribution control element 5 is formed on the wafer 1. By use of a cylindrical lens as the collector lens 6, the above-described operation is applied only to one axis, illumination light is converged along the other axial direction, and the illuminance distribution corresponding to the transmittance and phase distributions provided from the illuminance distribution control element 5 is imparted to the scan direction S2. Thereby, only a short area along the scan direction S1 can be illuminated. In the case where the laser beam emitted by the laser light source 2 is substantially a gaussian beam and the illuminance distribution control element 5 is not specifically operated, a gaussian distribution that is determined by the beam expander 7 and the collector lens 6 is projected onto the wafer.

As members exhibiting a fixed transmittance or phase distributions to be imparted, there are, for example, a diffraction optical element (DOE), a homogenizer (formed from a microlens array, an optical fiber handle, or a hollow pipe having an interior coated with a reflective coating (FIG. 9E). The configuration is formed to connect a controller 14 that is controlled by the total control section 53 and to use a spatial light modulator (SLM) so that the illuminance distribution control element 5 is dynamically variable. Thereby, before and after or during scan of the illuminated area 20 on the wafer 1, the illuminance distribution is dynamically controlled and adjusted to have an arbitrary shape. As examples of the dynamically variable spatial light modulator, there are elements of transmission and reflection types. The transmission-type elements include, for example, a liquid crystal element and a magnetooptical spatial light modulator. The reflection-type elements include, for example, a digital micromirror device (DMD), a grating valve (GLV), and a reflection liquid crystal element such as a LOCOS (liquid crystal on silicon) element. The configuration can be formed by selecting an appropriate one of these elements.

The illuminance distribution is monitored by the review optical system 104, which is described further below. The monitoring enables correction for various things, in addition to the control of the illuminance distribution. The correction can be implemented through regulation of the illuminance distribution control element 5, thereby to correct for, for example, misalignments of the illuminance distribution caused due to the aberrations and misalignments of the optical elements included in the optical system 101. Further, even when dynamic fluctuations have occurred in, for example, misalignment distortion, and turbulence in the illuminance distribution due to environmental changes, correction therefor can be implemented through the regulation of the dynamically variable spatial light modulator.

FIG. 10 includes FIGS. 10A to 10F showing example illuminance distributions formed in the configurations described above. In the on-wafer illuminated area 20 ("on-wafer . . . "hereinbelow will be used to express" . . . on the wafer"), the illuminance distribution is imparted inclinations or positional dependencies along the scan direction S2 as shown in FIG. 10. Thereby, even when detecting a same defect, intensive scattered light is incident on a pixel present in a point conjugate with a high illuminance portion. Hence, while a large signal can be acquired from the pixel, weak light is incident on the pixel present at the point conjugate with the high illuminance portion, so that a relatively small signal can be acquired from the pixel.

More specifically, the above corresponds to effectual detection of scattered light on a high sensitivity pixel and a low sensitivity pixel from the same defect. An equivalent effect can be achieved in the manner that the per-pixel sensitivity is differentiated by, for example, bonding an intensity filter onto the light receiving surface of the linear array sensor 9. The method of imparting the inclination or positional dependency to the illuminance distribution has an advantage in that adjustment and change in the angular distribution can be made through the regulation of the illuminance distribution control element 5.

According to the methods described above, the sensitivities of the respective pixels of the linear array sensor 9 are differentiated from one another. Then, signals acquired from those pixels and a sum signal of the signals is subjected to the processes, such as saturation determination and selective use, in the signal processor section 105 described further below, thereby to enable the high sensitivity, wide dynamic range inspection.

FIG. 10A is substantially a gaussian distribution reflective of the distribution of the laser light source 2.

FIG. 10B is an example of a substantially homogeneous illuminance distribution formed by use of a homogenizer as the illuminance distribution control element 5. The substantially homogeneous illuminance distribution is suitable to achieve high sensitivity inspection by maximizing scattered light occurring from a defect while suppressing thermal damage.

FIG. 10C is a distribution formed with a reduced central illuminance with respect to a homogeneous illuminance distribution. In the distribution of FIG. 10C, the temperature elevation occurring in the event of homogeneous distribution is maximized in the center of the illuminance distribution. Hence, in the case where there is a probability of causing thermal damage on the wafer, the distribution is suitable to achieve high sensitivity while preventing the thermal damage.

FIG. 10D is an example of an illuminance distribution that is maximized in units of the position corresponding to the respective pixel of the linear array sensor 9. Since the distribution effectually reduces in the area that is detected through the respective pixel, the distribution is effective to attenuate scattered light occurring from a wafer roughness portion potentially leading to be a noise factor. The maximum value of the illuminance in units of the respective pixel of the linear array sensor 9 does not have to be made identical, the maximum value may be changed in units of the respective corresponding position for obtaining the wide dynamic range.

FIG. 10E is a distribution suitable to effectually impart the sensitivity different in units of the respective pixel of the linear array sensor 9 by inclining the illuminance distribution. Further, the distribution is suitable to achieve the wide dynamic range detection while simplifying processing in the signal processor section 105 described further below. As shown in FIG. 10F, by imparting an exponential variation to the illuminance distribution, a further wide dynamic range can be achieved.

The on-wafer illuminance distribution formed by the illumination optical system 101 is measured by the review optical system 104. As shown in FIG. 1, the review optical system 104 is configured using the imaging system 81 and an image sensor 82.

The on-wafer position of irradiation formed by the illumination optical system 101 is magnified and image-formed by the imaging system 81 on the light receiving surface of the image sensor 82. In the event of performing oblique illumination through the illumination optical system 101, the image acquired in the image sensor 82 is a brightfield image, in which a brightness distribution of the acquired image as it corresponds to the on-wafer illuminance distribution formed by the illumination optical system 101. When the wafer surface condition is very smooth, scattering almost does not occur, so that measurement of the illuminance distribution by the image sensor 82 becomes difficult. In this case, the illuminance distribution is measured by placing a wafer treated to provide a rough surface or ceramic material having a rough surface is placed at the same height as that of the wafer surface. Alternatively, a high sensitivity image sensor having less noise, such as an electron multiplying charge coupled device (EMCCD) or electron bombardment CCD (EBCCD) or a cooled CCD may be used with an increased accumulation time period to enable the measurement.

Next, the configuration of the signal processor section 105 will be described below. Further, a defect determination method and defect coordinate and defect size calculation methods will be described below.

FIG. 11 shows the configuration of an analog processing section 51. Signal currents output from pixels 9a to 9d of the linear sensor 9 are, respectively, converted to voltages (voltage signals) and amplified by preamplifier sections 501a to 501d. Further, high frequency noise components of the signals are cut off by low pass filters 511a to 511d. Then, the signals are, respectively, converted to digital signals in analog-digital converter sections 502a to 502d having sampling rates sufficiently higher than cutoff frequencies of the low pass filters 511a to 511d, and the data signals are output. Here, the converted data signals respectively have sufficient bit depths to be not saturated in signal addition in a below-described digital processing section 52.

FIG. 12 shows the configuration of the digital processing section 52. Delaying sections 503a to 503d, respectively, include memories that accumulate signal outputs from the respective pixels for a time interval $\Delta t$ during which the illuminated area 20 makes one rotation on the wafer in operative association with scan S1.

The signal from the pixel 9a is delayed by the time interval $\Delta t$ in the delaying section 503a, and is added to the signal from the pixel 9b. This enables acquiring a signal equivalent to a signal acquired after two scan and detection operations are performed for the same portion on the wafer and the resultant signals are added together. Similarly, the signal acquired as above is delayed by the time interval $\Delta t$ in the delaying section 503b, and is then added to the signal the signal from the pixel 9c. This enables acquiring a signal equivalent to a signal acquired after three scan and detection operations are performed for the same portions on the wafer and the resultant signals are added together.

The configuration of the digital processing section 52 is formed to output signals G1 to G4. The signal G1 is a signal acquired in the manner that the signal output from the delaying section 503a is delayed by a time interval of "$2\times\Delta t$" in a delaying section 504a. The signal G2 is a signal acquired in the manner that the signal output from the delaying section 503b is delayed by the time interval $\Delta t$ in a delaying section 504b. The signal G3 is a signal output from the delaying section 503c. The signal G4 is a signal acquired as a result of the addition of the signal G3, which has been output from the delaying section 503c, and the signal output from the pixel 9d. Thus, the respective signal Gn (n=1, 2, 3, or 4) is equivalent to a signal acquired after n detection operations are performed for the same portion on the wafer and the resultant signals are added together.

The delaying sections 504a and 504b, respectively, collate the timings of appearance of the same portion signals corresponding to the signals G1 and G2 to the signal G3 and G4. The signals G1 to G4 are input into a determination processing section 505. While, in the present embodiment, the example case where the number of sensor pixels is four is shown for the sake of brevity, the configuration is not limited thereto. Even in the case of a sensor having a larger number of pixels (N pixels), the similar step is iterated, $\tilde{N}1$ delay additions are carried out, and timing shifts are corrected in the rear-side delaying sections, thereby to enable obtaining a signal equivalent to a signal acquired after 1, 2, . . . , N times of scan and detection operations are performed for the same portion, and the resultant signals are added together.

FIG. 13A shows a first example configuration of the determination processing section 505.

In the configuration of FIG. 13A, the signals G1 to G4 are input into a saturation determination section 601 and a signal selection section 602. It is now assumed that the sensitivities of the pixels 9a to 9d are differentiated from one another by the device described above, in which an effectual sensitivity of the pixel 9a is lowest, and the sensitivities are higher in the order of the pixel 9a to 9d. More specifically, where the effectual sensitivities of the pixels 9a, 9b, 9c, and 9d are, respectively, represented by Sa, Sb, Sc, and Sd, the relation "Sa<Sb<Sc<Sd" is established.

In the saturation determination section 601, the occurrence or nonoccurrence of saturation in the respective pixels 9a to 9d is determined in accordance with the signals G1 to G4. More specifically, the saturation determination is performed through comparison in a largeness/smallness relation between digital signal values corresponding to maximum signal output values of the respective pixels (9a to 9d) of the linear array sensor 9 and the differential values between digital signal values before and after the addition in the configuration shown in FIG. 12. For example, the output signal from the pixel 9a corresponds to the difference between the signal G2 and the signal G1. Hence, comparison is performed to determine whether the difference between the signals G2 and G1 is substantially equal to a maximum signal output value (saturation signal value) from the pixel 9a (for example, whether the difference is larger from a signal level corresponding to 90% of a saturation signal level) or smaller than the maximum signal output value. Thereby, it is determined whether the output signal of the pixel 9a is saturated. In the saturation determination section 601, determination is performed for output signals from the respective signals 9b, 9c, and 9d, and information of a saturation pixel. In the case where the saturation determination is performed in order of the pixels 9a, 9b, 9c in accordance with the relative relationship between the sensitivities of the respective pixels 9a to 9d and, as a result, it is determined that saturation has occurred in any one of the pixels. In this case, it is predicted that saturation occurs also in the subsequent pixels, such that subsequent saturation determination is not necessary. Hence, in this case, as saturation pixel information, it is sufficient to output either a number of the first pixel determined as a saturation pixel during the saturation determination for the pixels 9a to 9d or information indicating that saturation has not occurred in any one of the pixels.

The signals G1 to G4 and the saturation pixel information are input into the signal selection section 602. In the signal selection section 602, in accordance with the saturation pixel information input from the saturation determination section 601, a signal to which the signal of the saturation pixel has not been added is selected from among the signals G1 to G4, and is output as an optimum sensitivity signal 603a. Further, effectual sensitivity information is output as a sensitivity information signal 603b. The effectual sensitivity information is indicative whether the selected signal corresponds to a signal effectually acquired at which sensitivity. The sensitivity information signal 603b is used in post-processing to correct and calculate an absolute amount of a signal value practically detected at a different sensitivity and added. For example, in the event that the signal is determined by the saturation determination section 601 to have been saturated in the pixel 9c, the signal G2 before the output from the pixel 9c is added is selected and output in the signal selection section 602. Further, since the signal G2 is the signal to which the signals from the pixels 9a and 9b, the value "Sa+Sb" is output as the sensitivity information signal 603b taking into account the influences of the per-pixel sensitivity and the addition. As the optimum sensitivity signal 603a, even when any one of the signals G1 to G4 is selected, a signal value corresponding to the largeness/smallness of the original defect scattered amount can be acquired by dividing the signal value by the value of the signal 603b.

After having been subjected to an extraction process of a high pass filter 604a to extract a defect signal, the optimum sensitivity signal 603a is input into a defect determination section 605a. Because the defect is scanned by the illuminated area 20 along the direction S1, the waveform of the defect signal corresponds to a magnified/reduced illuminance distribution profile in the direction S1 of the illuminated area 20. A frequency band including the defect signal waveform is passed through the high pass filter 604a, and the frequency band containing relatively much noise and DC (direct current) components are cut off, thereby to improve the S/N ratio of the defect signal.

As the high pass filter 604a, any one of the following filters may be used. The filters are a high pass filter designed to have a specific cutoff frequency and thereby to cut off components having frequencies higher than or equal to the frequency or a FIR filter analogous to the waveform of the defect signal. The defect determination section 605a performs a thresholding process of the input of the signal including the defect waveform output from the high pass filter 604a, thereby to determine of the presence or absence of a defect. For a portion determined as a defect-present portion, the defect coordinate indicative of the defect position in the wafer and an estimated value of the defect size are output in accordance with the defect waveform and the sensitivity information signal 603b.

For obtaining the defect coordinate, there is a method of performing calculation thereof in accordance with the center of gravity of the waveform. For obtaining the defect size, there is a method of performing calculation thereof in accordance with the integral value of the defect waveform. By use of the optimum sensitivity signal 603a and the sensitivity information signal 603b, any of the methods is able to perform the calculation without being influenced by the saturation signal in accordance with the signal accurately corresponding to the largeness/smallness in amount of scattered light occurring from the defect. Consequently, the defect coordinate and size can be obtained with high accuracy.

A maximum sensitivity signal 611, that is, a signal with a highest effectual sensitivity, which corresponds to the signal G4 here in the present case, is input into a low pass filter 604b, and a low frequency component and DC component are output therefrom. The output from the low pass filter 604b corresponds to an amount of scattered light (haze) from a microroughness portion in the illuminated area 20 on the wafer. Ordinarily, the attenuator 3 in the illumination optical system 101 is regulated to prevent the linear array sensor 9 from being saturated by the DC component of the signal. Even in the case of the signal G4 having the highest effectual sensitivity, there is no risk that a saturation signal is contained therein, so that the signal G4 not being subjected to the saturation determination is input into the low pass filter 604b. Of course, the configuration may be formed to permit the inputting of a signal 603a that has been determined by the saturation determination to not contain a saturation signal. According to this configuration, even in the case where the low frequency compositional component is increased by a local increase in the roughness of a roughness portion, saturation can be prevented.

The output of the low pass filter 604b is then output into a haze processing section 605b, and haze information is processed therein. In accordance with the level of the input signal, the haze processing section 605b outputs either a signal corresponding to the haze level or information corresponding to a spatial frequency of the roughness portion as a haze signal 606b.

A second example configuration of the determination processing section 505 will be described herebelow with reference to FIG. 13B, focusing on portions different from those shown in FIG. 13A.

In the second example configuration, the maximum sensitivity signal 611 is input into the high pass filter 604a. When the optimum sensitivity signal 603a is input as in the configuration of FIG. 13A, a case can take place where a sawtooth shape is caused in the waveform of the optimum sensitivity signal 603a due to a momentary variation in the event of switching from a sensitivity signal to another sensitivity signal. In this case, such a defective shape is not eliminated in the high pass filter 604a and is input as a distortional waveform or unnecessary noise into the defect determination section 605a, thereby to lead to, for example, reduction in the defect coordinate calculation accuracy and erroneous detection.

However, according to the configuration of FIG. 13B, the maximum sensitivity signal 611 is all time input into the high pass filter 604a, and the output thereof is input into the defect determination section 605a, thereby to perform the defect determination. Hence, an even more robust defect determination is performed without being influenced by switching between selective signals. In this case, however, while a saturation signal can be determined as a defect, it is difficult to perform the defect size calculation in accordance with the level (largeness/smallness) of the defect signal. To overcome this problem, the optimum sensitivity signal 603a and the sensitivity information signal 603b are input into a defect size determination section 613. Then, for a portion determined as a defect by the defect determination section 605a, the defect size is calculated in accordance with the corresponding optimum sensitivity signal 603a and sensitivity information signal 603b. The defect size determination is performed using the optimum sensitivity signal 603a and the sensitivity information signal 603b. Thereby, the high-accuracy defect size can be obtained without being influenced by the saturation signal in accordance with the signal accurately corresponding to the largeness/smallness in amount of scattered light from the defect.

In the defect size determination section 613, the defect coordinate calculation may be performed in addition to the defect size determination. Thus, according to the configuration shown in FIG. 13B, the robust defect determination and the high-accuracy defect coordinate and size calculation can be compatibly accomplished.

A detection dynamic range expansion method using signals associated with mutually different effectual sensitivities and a defect size calculation method in accordance therewith will be described below with reference to FIG. 14.

FIG. 14A shows the relation between the amount of scattered light received by the linear sensor 9 and the magnitudes of respective signals when detected in a high sensitivity pixel, an intermediate sensitivity pixel, and a low sensitivity pixel. Detection performed in the manner that mutually different levels of illuminance are provided to per-pixel detection positions on the wafer, and the detection is performed for pixels having the same sensitivity is substantially equivalent to the detection of the pixels having mutually different levels of illuminance.

As shown in FIG. 14A, in the case of only one type of pixel sensitivities (only high sensitivity pixels), the range of the amount of scattered light detectable in a dynamic range R of the detector device is formed as a range represented by R1. However, when pixels having multiple sensitivities are combined, detection can be performed over an even wider detection light amount range R2.

With reference to FIG. 14B, when the linearity of the responses (response signals) is maintained within the dynamic range R of the detector device, linear response signals can be obtained in a wide range shown as the light amount range R2. Assume that a dynamic range D is a ratio $i2/i1$, where $i1$ and $i2$, respectively, are minimum and maximum detection light amounts to be obtained by the linear array sensor 9. In this case, an amount of scattered light greater or equal to $i1$ and smaller than or equal to $i2$ is detected through the high sensitivity pixel. In addition, an amount of scattered light greater or equal to "$i1 \times D$ ($=i2$)" and smaller than or equal to "$i2 \times D$" is detected through the intermediate sensitivity pixel having a sensitivity $1/D$ times the sensitivity of the high sensitivity pixel. Further, an amount of scattered light greater or equal to "$i1 \times (D^2)(=i2 \times D)$" and smaller than or equal to "$i2 \times D^2$" is detected through the low sensitivity pixel. Thereby, the amounts of scattered light in the range of $i1$ or greater to "$i2 \times D^2$" or smaller can be detected, and the dynamic range is expanded to $D^2$ times. Hence, when, as shown in FIG. 14B, N (pieces of) detection pixels corresponding to the dynamic range D are each imparted a D-times mutual difference in sensitivity, and response curved lines are connected together, a dynamic range of the Nth power of D can be realized.

FIG. 14C is a graph showing that calculation of the sizes of defects in a wide size range is enabled through an expanded dynamic range. The amount of scattered light of a particle having a diameter of 500 nm is approximately $10^6$ times (120 dB) the amount of scattered light of a particle having a diameter of 20 nm. Now assume that the dynamic range of the respective pixel of the linear array sensor 9 is 50 dB, and relative to the high sensitivity pixel, the sensitivity of the intermediate sensitivity pixel is −35 dB and the sensitivity of the low sensitivity pixel is −70 dB. In this case, an overall range of 120 dB can be covered, and amounts of signal light of particles having diameters ranging from 20 nm to 500 nm can be measured. Consequently, high accuracy size calculations can be performed over the particle diameter range can be performed in accordance with the correlation between the amount of signal light and the particle diameter, as shown in FIG. 14C.

A modified example of the embodiment described above will be described below. Only portions different from those of the above-described embodiment will be described herebelow with reference to FIGS. 15 and 16.

FIG. 15A shows a case where illumination light in multiple mutually different azimuths or incident angles or illumination light in multiple mutually different polarized states is irradiated on the wafer. An illuminated area 20a (illumination azimuth I1) and illuminated area 20b (illumination azimuth I2) associated with the mutually different rays of illumination light correspond to pixels in mutually different conjugate positions of the linear array sensor 9. The illumination light such as described above is implemented by separating the optical path of the illumination optical system 101 into multiple optical paths each provided with an optical section that regulates beam paths or shapes or illumination distributions of various devices. The various devices include, but not limited to, a beam expander, an illuminance distribution control element, collecting lens, and a reflection mirror.

FIG. 15B shows the configuration of the linear array sensor 9 that detects only longitudinal polarized components in pixels 9a and 9b and only transverse polarized components in pixels 9c and 9d. A polarizing filter 901 is disposed in front of the linear array sensor 9. The polarizing filter 901 is configured from a micro-polarizing element array including micro-polarizing elements 901a and 901b that selectively transmit mutually different polarized components. Creation methods for such micro-polarizing elements include a method of the type in which a thin film polarizing plate having a micron to submicron order thickness is overlaid on an imaging device or substrate, and unnecessary portions are removed by etching to meet with the size of the pixel. Then, a thin film polarizing plate or wavelength plate in which a primary axis azimuth (direction) is different is further overlaid, and similar patterning is iteratively performed. However, the creation method is not limited to the above-described method, and may be the type in which a small or micro-grating having a periodicity shorter than a wavelength of light being used is created by patterning, thereby to impart an optical anisotropy in units of the pixel.

It is now assumed that, in the method shown in FIGS. 15A and 15B, illumination or detection is performed under mutually different optical conditions, and signals of scattered light occurring under the respective optical conditions can be obtained for a defected. In this case, as shown in FIG. 15C, responses to the optical conditions are plotted in a multidimensional space, and the types of defects can be classified in accordance with distributions in the space. For example, illumination is provided in the manner that low-angle (large incident angle) illumination or P-polarized illumination is set as an optical condition A, and high-angle (small incident angle) illumination or S-polarized illumination is set as an optical condition B. In this case, the illumination under the optical condition B causes the illumination light to penetrate relatively deeper into the wafer surface or a film formed thereon. Hence, scattered light from a respective defect (defect type 2) present inside the surface is more intensive under the optical condition B, and scattered light from a respective defect (defect type 1), such as a foreign matter, present upward of the surface is relatively intensive under the optical condition A. Hence, distributions of scattered signals are formed as shown in FIG. 15C, and defect type classification is performed in accordance with the signal distributions. Similarly, differences in scattered responses associated with the difference in the optical condition depending on the defect sizes can be observed, so that, the accuracy of the defect size calculation can be improved in a method similar to the above.

FIG. 16 shows the configuration of the digital processing section 52 for implementing the defect classification or defect size calculation method shown in FIG. 15. The signals obtained under the optical conditions A and B are added and regulated in timing by the configuration formed from the delaying sections 503a, 503c, 504a, and 504b. Thereafter, signals 621a to 621d are input into the determination processing section 505.

Subsequently, the signals input into the determination processing section 505, namely the signals 621a and 621b under the optical condition A and the signals 621c and 621d under the optical condition B, are then input into the signal selection section 602, as shown in FIG. 16B. In the saturation determination section 601, saturation determinations are performed in the same manner as that performed in the saturation determination section 601, as described with reference to FIG. 13, for the respective signals under the optical conditions A and B. Thereby, saturation pixel information is output corresponding to the respective optical condition.

The saturation pixel information in units of the respective optical condition and each of the signals 621a to 621d is input into the signal selection section 602. In the signal selection section 602, a not-added one of the multiple signals is selected in accordance with the respective input in units of the optical condition, and the signal is output as each respective optimum sensitivity signal 623a, 623b, and sensitivity information of the respective selected signal is output as the signal 603b (sensitivity information signal).

From the respective per-optical condition optimum sensitivity signals 623a and 623b, defect signals are extracted by high pass filters 624a and 624c, and haze signals are extracted by low pass filters 624b and 624d. The per-optical condition defect signals output from the respective high pass filters 624a and 624c and the corresponding sensitivity information signal 603b are input into a defect determination section 625a. Similarly, the per-optical condition haze signals output from the respective high pass filters 624b and 624d and the corresponding sensitivity information signal 603b are input into a haze processing section 625b. In the defect determination section 625a, the thresholding process is performed for the per-optical condition defect signals, defect candidate positions are detected, and an OR thereof is derived, thereby to detect the defect position.

Thus, the defect detection is performed in accordance with the signals of the multiple optical conditions, so that there is an advantage in that the defect trapping rate is relatively higher as compared to the case of defect detection performed in accordance with a single condition.

Further, in the defect determination section 625a, the defect classification or defect size calculation method shown in FIG. 15 is performed using the per-optical condition defect signals. In the haze processing section 625b, a signal corresponding to the haze magnitude or information corresponding to the spatial frequency of the roughness portion is output as a haze signal 626b in accordance with the per-optical condition haze signals. The dependency on the optical condition, such as illumination incident angle, azimuth angle, or polarization is different depending on, for example, the roughness RMS value, spatial frequency, and the like. Hence, roughness information in more detail than that in the case under a single optical condition can be obtained through the process performed in accordance with the haze signal.

Next, a defect detection process flow will be described herebelow with reference to FIG. 18.

First, as recipe specifications for specifying a recipe, an inspection condition including, for example, the illumination direction and sensor sensitivity, is specified (at step 120). The recipe specifications further include specifications of the length of the illuminated area 20 in one of the directions S1 and S2, a distance Δr thereof in the scan direction in the scan direction S2, and a processing method(s) to be carried out for detected scattered light.

Subsequently, a wafer scan is started (at step 21), and signal processing specified in the recipe is executed (at step 122). The defect determination is performed in accordance with processed signals (at step 123), and the inspection results, such as a defect map (diagram showing a distribution of defect positions in the wafer) are displayed on the display section 54 (at step 124). In addition to the defect map, the inspection results to be displayed include, for example, the number of defects, the number of defects in units of the defect size, the number of defects in units of the defect type, a defect map in units of the defect size or type, and a distribution of haze in the wafer.

FIG. 19 shows one example of a user interface for displaying recipe specifications and inspection results. Configuration elements include a defect map 130 to be displayed after completion of the inspection, and subwindows for specification of inspection modes prior to the inspection. The defect map is displayed in accordance with items acquired in the inspection, including defect signals, defect sizes, and defect types, and coordinates. Also display switching to the map showing the haze distribution can be one of a configuration item by necessity.

The inspection mode 131 can be selected through either direct input or pulldown selection. The number of operations of illumination on the same defect during one operation of the inspection does not have to be the same. For example, the inspection mode can be set to a standard mode (132) for the inspection of an inner circumference portion of a sample, and can be set to a high sensitivity mode (133) for the inspection in an outer circumference portion of the sample. For example, in the high sensitivity mode, the distance Δr is reduced, and the number of operations of illumination is increased, thereby to enable the detection sensitivity to be improved.

As described above, according to the embodiment of the present invention, multi-time illumination is provided to the same defect in the single operation of inspection, and multiple rays of scattered light occurring therefrom are added together. Consequently, the detection sensitivity can be improved.

Further, the inspection can be performed without reducing throughput by use of the photodiode array including multiple pixels. According to the embodiment of the present invention, the inspection method and apparatus capable of compatibly accomplishing detection sensitivity improvement and high throughput can be realized.

Further, the configuration uses signals acquirable from multi-time illumination with mutually different illuminances or multi-time detection through pixels having mutually different sensitivities. Thereby, dynamic range expansion, high-accuracy defect size determination, and high-accuracy defect coordinate calculation can be implemented. Further, defect classification performance can be improved by use of the signals acquired through the multi-time detection under the mutually different optical conditions (illumination condition or detection condition).

As above, while the invention made by the present inventors has been described in detail in accordance with the embodiments, the present invention is not limited thereto, and various changes and modifications may be made without departing from the scope and spirit of the invention. Further, the defect inspection apparatus and method may, of course, be configured by combining the respective embodiments of the configurations.

According to the present invention, a defect inspection method and apparatus capable of performing detection of defects having small to large sizes and size calculation therefor can be provided.

The invention claimed is:

1. A defect inspection apparatus for inspecting a surface of a sample, comprising:
   a stage for holding the sample and for moving the sample in a rotational direction and in a translational direction;
   an illumination optical system that irradiates a laser beam to form a linear illuminated area on the surface of the sample;
   a detection optical system that includes a detector device including a plurality of pixels for detecting light scattered from the linear illuminated area of the surface of the sample, the plurality of pixels having different sensitivity values with respect to one another for the detected light, and that transforms a plurality of the scattered light detected by the plurality of pixels of the detector device having the different sensitivity values to a plurality of detection signals; and
   a signal processing system that selects an unsaturated detection signal from the plurality of detection signals detected by the pixels of the detector device having the different sensitivity values from a same area of the surface of the sample and that detects a defect on the surface of the sample in accordance with the selected unsaturated detection signal;
   wherein at least one of the illumination optical system and the detection optical system provide mutually different optical conditions for at least one of illumination and detection, and the plurality of pixels of the detector have different responsiveness set in accordance with the mutually different optical conditions for the at least one illumination and detection.

2. A defect inspection apparatus as defined in claim 1, wherein the plurality of detection signals are output in parallel from the detection optical system and are, respectively, based on the scattered light detected through multi-time illumination provided onto the same area of the surface of the sample.

3. A defect inspection apparatus as defined in claim 1, wherein the illumination optical system irradiates the laser beam so that an illuminance distribution in the linear illuminated area of the surface of the sample has an inclination.

4. A defect inspection apparatus as defined in claim 1, wherein the illumination optical system irradiates the laser beam so that an illuminance distribution in the linear illuminated area of the surface of the sample includes a distribution maximized in units of a position corresponding to the plurality of pixels of the detector device having the different sensitivity values.

5. A defect inspection apparatus as defined in claim 1, wherein the illumination optical system irradiates the laser beam so that an illumination incident angle is 75 degrees or greater with respect to the surface of the sample.

6. A defect inspection apparatus as defined in claim 1, wherein an optical axis of the detection optical system is present in a plane substantially perpendicular to a longitudinal direction of the linear illuminated area.

7. A defect inspection apparatus as defined in claim 1, further comprising an oblique detection system having an optical axis inclined from a direction substantially perpendicular to the longitudinal direction of the linear illuminated area.

8. A defect inspection apparatus as defined in claim 1, wherein the signal processing system calculates a defect size by using the selected unsaturated detection signal.

9. A defect inspection apparatus as defined in claim 1, further comprising a review optical system that monitors the illuminance distribution in the linear illuminated area of the surface of the sample.

10. A defect inspection apparatus as defined in claim 1, wherein the signal processing system counts a number of the selected unsaturated detection signals detected from each area of the surface of the sample and detects a defect using the number of the selected unsaturated detection signals.

11. A defect inspection apparatus as defined in claim 1, wherein the plurality of pixels of the detector device having the different sensitivity values have the different sensitivity values with respect to one another in response to the same light scattered from the linear illuminated area of the surface of the sample which is detected.

12. A defect inspection apparatus as defined in claim 1, wherein the plurality of pixels of the detector device having the different sensitivity values have the different sensitivity values for the light scattered from the linear illuminated area of the surface of the sample independent of the color of the light.

13. A defect inspection apparatus as defined in claim 1, wherein the signal processing system selects the unsaturated detection signal from the plurality of detection signals and includes a saturation determination section which determines occurrence of saturation and non-saturation in signals of the respective pixels.

14. A defect inspection apparatus as defined in claim 13, wherein the saturation determination section includes a comparator enabling comparison in a largeness/smallness relation.

15. A defect inspection apparatus as defined in claim 1, wherein the plurality of pixels of the detector having the different sensitivity levels are arranged in a row and the different sensitivity levels of the respective pixels in the row are set so that a pixel at one end of the row has the lowest sensitivity level and a sensitivity level at the opposite end of the row has the highest sensitivity level and the pixels at intermediate positions in the row having the sensitivity levels increasing in a direction from the pixel having the lowest sensitivity level to the pixel having the highest sensitivity level at the opposite end of the row.

16. A defect inspection apparatus as defined in claim 1, wherein the mutually optical conditions for the at least one of illumination and detection which are set for the plurality of pixels of the detector device are mutually different optical conditions for the illumination in which the mutually different illumination optical conditions are illuminated areas associated with mutually different rays of illumination light corresponding to the plurality of pixels of the detector device which are arranged in mutually different conjugate positions.

17. A defect inspection apparatus as defined in claim 1, wherein the mutually different optical conditions for the at least one of illumination and detection which are set for the plurality of pixels of the detector device are mutually different optical conditions for illumination in which illumination lights are provided with multiple mutually different at least one of azimuth angles, incident angles and polarized states, and the responsiveness of the plurality of pixels of the detector are set in accordance therewith.

18. A defect inspection apparatus as defined in claim 1, wherein the mutually different optical conditions for the at least one of illumination and detection which are set for the plurality of pixels of the detector device are mutually different optical conditions for detection which are set so that the plurality of pixels of the detector device selectively detect mutually different polarized components.

* * * * *